(12) United States Patent
Tovar et al.

(10) Patent No.: US 10,040,067 B2
(45) Date of Patent: Aug. 7, 2018

(54) DEVICE AND METHOD FOR EXTRACTING INDIVIDUAL PICOLITER DROPLETS FROM MICROFLUIDIC EMULSIONS FOR FURTHER ANALYSIS AND SCALE-UP

(71) Applicant: Leibniz-Institut für Naturstoff-Forschung und Infektionsbiologie—Hans-Knöll-Institut, Jena (DE)

(72) Inventors: Miguel Tovar, Jena (DE); Emerson Zang, München (DE); Thomas Weber, Jena (DE)

(73) Assignee: LEIBNIZ-INSTITUT FÜR NATURSTOFF-FORSCHUNG UND INFEKTIONSBIOLOGIE—HANS-KNÖLL-INSTITUT, Jena (DE)

( * ) Notice: Subject to any disclaimer, the term of this patent is extended or adjusted under 35 U.S.C. 154(b) by 231 days.

(21) Appl. No.: 14/937,672

(22) Filed: Nov. 10, 2015

(65) Prior Publication Data
US 2016/0129443 A1 May 12, 2016

(30) Foreign Application Priority Data
Nov. 10, 2014 (DE) .................. 10 2014 116 357

(51) Int. Cl.
*B01L 3/00* (2006.01)
*G01N 35/10* (2006.01)
(Continued)

(52) U.S. Cl.
CPC ....... *B01L 3/502761* (2013.01); *B01L 3/0268* (2013.01); *G01N 15/1484* (2013.01);
(Continued)

(58) Field of Classification Search
CPC ......... B01L 2200/27; B01L 2200/0652; B01L 2200/0673; B01L 2200/10;
(Continued)

(56) References Cited

U.S. PATENT DOCUMENTS 5,515,466 A  5/1996  Lee
5,638,474 A  6/1997  Lampert et al.
(Continued)

FOREIGN PATENT DOCUMENTS

WO  WO 02/068104 A1  9/2002
WO  WO 2004/088314 A1  10/2004
(Continued)

OTHER PUBLICATIONS

Butler, P.A.G. et al. 1997 "Capillary Electrophoresis Detector Using a Light Emitting Diode and Optical Fibres" *Analyst* 122: 949-953.
(Continued)

*Primary Examiner* — Jennifer Wecker
(74) *Attorney, Agent, or Firm* — Knobbe, Martens, Olson & Bear, LLP (57) ABSTRACT

The disclosure relates to a method and a system for the isolation of picoliter droplets from a continuous stream of carrier fluid in a microfluidic system. In particular the disclosure relates to a system that comprises a sorter, a detector and a collector. The sorter serves for a selection of picoliter droplets with a desired content based upon an optical signal obtained from the picoliter droplets. The selected picoliter droplets are guided towards the detector that comprises a detection channel that is arranged perpendicular to a light beam. By means of a photodetector that is aligned with the optical axis of the light beam the passage of the picoliter droplets can be detected. The collector comprises multiple wells and the detection of the passage of the picoliter droplets results in a relative movement of the
(Continued)

detector and a collector such that the picoliter droplet is isolated by depositing it into one of said wells. The disclosure moreover relates to a method that uses such a system to isolate individual picoliter droplets. In particular the disclosure relates to a method that allows for an analysis and/or further processing of the content of the picoliter droplets that have been isolated from a microfluidic system by depositing them into a well.

18 Claims, 5 Drawing Sheets

(51) Int. Cl.
*B01L 3/02* (2006.01)
*G01N 15/14* (2006.01)
*C12M 1/00* (2006.01)
*C12M 1/12* (2006.01)

(52) U.S. Cl.
CPC ... *B01L 3/502784* (2013.01); *B01L 2200/027* (2013.01); *B01L 2200/0652* (2013.01); *B01L 2200/0673* (2013.01); *B01L 2200/10* (2013.01); *B01L 2200/143* (2013.01); *B01L 2300/0654* (2013.01); *B01L 2300/0819* (2013.01); *B01L 2300/0838* (2013.01); *B01L 2400/0424* (2013.01); *B01L 2400/0487* (2013.01); *C12M 25/01* (2013.01); *G01N 35/1011* (2013.01); *G01N 2015/149* (2013.01); *G01N 2035/1034* (2013.01); *G01N 2035/1044* (2013.01)

(58) Field of Classification Search
CPC ....... B01L 2200/143; B01L 2300/0654; B01L 2300/0819; B01L 2300/0838; B01L 2400/0424; B01L 2400/0487; B01L 3/0268; B01L 3/502761; B01L 3/502784; C12M 25/01; G01N 15/1484; G01N 2015/149; G01N 2035/1034; G01N 2035/1044; G01N 35/1011
See application file for complete search history.

(56) References Cited

U.S. PATENT DOCUMENTS

| | | | |
|---|---|---|---|
| 8,277,757 B2 | 10/2012 | Kelly et al. | |
| 8,765,455 B2 | 7/2014 | Beer et al. | |
| 2003/0027225 A1* | 2/2003 | Wada | B01L 3/50273 435/7.21 |
| 2003/0148531 A1 | 8/2003 | Hatcher et al. | |
| 2007/0146704 A1* | 6/2007 | Schmidt | B01L 3/502715 356/338 |
| 2008/0286751 A1 | 11/2008 | Renaud et al. | |
| 2010/0105112 A1 | 4/2010 | Holtze et al. | |
| 2010/0136544 A1 | 6/2010 | Agresti et al. | |
| 2012/0108721 A1 | 5/2012 | Mazutis | |
| 2013/0095469 A1 | 4/2013 | Koltay et al. | |
| 2013/0210639 A1* | 8/2013 | Link | B01F 3/0807 506/2 |
| 2013/0213488 A1 | 8/2013 | Weitz et al. | |
| 2013/0217601 A1 | 8/2013 | Griffiths et al. | |
| 2013/0319861 A1* | 12/2013 | Khandros | B81B 1/00 204/452 |
| 2014/0021049 A1 | 1/2014 | Joaquim et al. | |
| 2014/0323317 A1 | 10/2014 | Link et al. | |
| 2015/0049333 A1* | 2/2015 | Gourley | G01N 15/1484 356/338 |

FOREIGN PATENT DOCUMENTS

| | | |
|---|---|---|
| WO | WO 2005/089921 A1 | 9/2005 |
| WO | WO 2006/005923 A1 | 1/2006 |
| WO | WO 2009/011808 A1 | 1/2009 |
| WO | WO 2010/042744 A1 | 4/2010 |
| WO | WO 2010/151776 A2 | 12/2010 |

OTHER PUBLICATIONS

Cao, Z. et al. 2013 "Droplet sorting based on the number of encapsulated particles using a solenoid valve" *Lab on a Chip* 13: 171-178.

Leung, S.-A. et al. 2004 "Continuous real-time bubble monitoring in microchannels using refractive index detection" *Meas Sci Technol* 15: 290-296.

Martin, K. et al. 2003 "Generation of larger number of separated microbial populations by cultivation in segmented-flow microdevices" *Lab Chip* 3: 202-207.

Bai, et al. 2014 "Interfacing picoliter droplet microfluidics with addressable microliter compartments using fluorescence activated cell sorting" *Sensors and Actuators B* 194: 249-254.

Baret, et al. 2009 "Fluorescence-activated droplet sorting (FADS): efficient microfluidic cell sorting based on enzymatic activity" *Lab Chip* 9(13): 1850-1858.

Debs, et al. 2012 "Functional single-cell hybridoma screening using droplet-based microfluidics" *Proceedings of the National Academy of Sciences* 109(29): 11570-11575.

Küster, et al. 2013 "Interfacing droplet microfluidics with matrix-assisted laser desorption/Ionization mass spectrometry: label-free content analysis of single droplets" *Analytic Chemistry* 85: 1285-1289.

Mazutis, et al. 2013 "Single-cell analysis and sorting using droplet-based microfluidics" *Nature Protocols* 8(5): 870-891.

Najah, et al. 2014 "Droplet-based microfluidics platform for ultra-high-throughput bioprospecting of cellulolytic microorganisms" *Chemistry & Biology* 21: 1722-1732.

Zang, et al. 2013 "Real-time image processing for label-free enrichment of Actinobacteria cultivated in picolitre droplets" *Lab Chip* 13: 3707-3713.

\* cited by examiner

DEVICE AND METHOD FOR EXTRACTING INDIVIDUAL PICOLITER DROPLETS FROM MICROFLUIDIC EMULSIONS FOR FURTHER ANALYSIS AND SCALE-UP

FIELD OF THE INVENTION

The field of the invention is droplet-based microfluidics, which has been rapidly developing in recent years as an efficient tool for high throughput analysis of biological variants. It allows reproducible compartmentation of biological materials such as molecules or cells in separate droplets with the effect of saving time and costs in further process steps.

BACKGROUND

Droplet-based technologies were developed in recent years by applying existing technologies. Functional units include production (WO2002/068104 A1, WO2005/089921) and storage (WO2010/042744 A1), droplet splitting and fusion (US2012/0108721 A1), injection of additional reagents (WO2010/151776 A2), and deflection/sorting (U.S. Pat. No. 8,765,455 B2, US 20130213488 A1).

As an example, one may attempt to select particular individual microorganisms out of a population of millions of microorganisms with respect to a specific activity (e.g. growth rate or biosynthesis of a product). In the classic approach, the cell population is distributed in a suitable solution over a solid nutrient medium and isolated in this way. The individual colonies that have grown are examined after a variable incubation phase which can typically last from days to weeks. This step of cultivating and harvesting large numbers of individual colonies is very time-consuming and cost-intensive. Advanced robot systems can bring significant time savings to this task, but the amount of working hours needed is still immense. Droplet-based microfluidics, however, is a suitable tool for solving this issue. In this case the microorganisms are spatially separated from one another in aqueous droplets of variable size. In combination with a surfactant and an oil phase located outside the droplet, such emulsion droplets, typically in the picoliter range can be handled easily. They can be analyzed in a continuous microfluidic flow using currently available technology. The droplets with the microorganisms can be sorted at rates in the kilohertz range (Baret et al., Lab-on-a-Chip 2009, 9, 1850-1858).

The resulting effects to use aqueous droplets after sorting have however been inefficient in the prior art, because individual extraction is difficult to handle. In the prior art the microfluidic droplets are collected and the aqueous phases of all droplets are combined using emulsion dissolving agents. Thereby the content of the droplets is separated from the oil phase and the enclosed cells are recultivated as a whole (Mazutis et al., Nature Protocols, 2013, pp. 870-891, Najah et al., Chemistry & Biology 2014, Vol 21/12, pp. 1722-1732, Debs et al., PNAS, 2012, Vol. 109, pp. 11570-11575, and others). A retrieval of a single unlabeled aqueous emulsion droplet in the picoliter volume range is not possible with methods or devices of the prior art.

Bai et al. in 2014 describe a high throughput sorting and depositing of agarose droplets by a FACS (fluorescence activated cell sorter), (Y. Bai et al., Sensors and Actuators B: Chemical, 2014, 194, pp. 249-254). This approach has however several disadvantages. It requires the use of gel-like droplets and the purchase of very expensive FACS devices. Moreover, sorting in the case of FACS necessitates the use of fluorescent markers expressed and localized at sufficient levels within the single cells, further limiting the biological applications of these devices.

A system has been published that detects aqueous droplets in a continuous oil phase within a capillary and deposits them on a MALDI (matrix assisted laser desorption ionization) plate (Küster et al., Analytical Chemistry, 2013, 85, pp. 1285-1289). However, in this case only large droplets of a minimal size of 3 nl can be isolated and the method is restricted to the deposition of periodically generated droplets. Moreover the subsequent analysis of the droplets is restricted to mass spectroscopy in which the biological content is typically destroyed.

In the prior art it has therefore not been possible to isolate individual microfluidic emulsion droplets on the picoliter scale from a droplet pool in a microfluidic system especially when droplets are produced for an isolation at varying irregular frequencies. Moreover a subsequent cultivation of target organisms that have been encapsulated in a microfluidic emulsion droplet outside the microfluidic system has also not been possible.

SUMMARY OF THE INVENTION

The objective of embodiments of the invention was therefore to provide a system and a method that overcomes the disadvantages of the prior art and allows for an efficient isolation of microfluidic droplets on the picoliter scale. In particular a task of the embodiments of the invention was to design a system and a method that is capable of selecting single microfluidic droplets from a pool of droplets for a subsequent analysis and/or scale up of the content of the droplet outside of a microfluidic system.

The objective is achieved by a method and a system according to the independent claims. The dependent claims of the method and the system cover preferred embodiments of the inventions.

Embodiments of the invention therefore relate to a system for isolating picoliter droplets comprising
  a) a sorter comprising a microfluidic chip configured for the passage of picoliter droplets and their selection based upon an optical signal obtained from the picoliter droplets,
  b) a detector comprising a detection channel with an inner cross-sectional dimension smaller than 150 µm, a first light source generating a light beam and a first photodetector, wherein the detection channel is arranged perpendicular to the optical axis of the light beam in between the first light source and the first photodetector and
  c) a collector comprising multiple wells,
wherein the detector and the collector are configured to move in relation to each other based upon a signal generated at the first photodetector.

DETAILED DESCRIPTION OF CERTAIN EMBODIMENTS

Without intending to be limiting, the embodiments of the invention are explained in more detail with reference to exemplary embodiments.

With the system according to some embodiments of the invention it is possible to isolate individual microfluidic droplets on the picoliter scale for subsequent analysis and/or a scale up of the content of the droplet. The selection of the microfluidic droplets using the sorter advantageously enables to select one single picoliter droplet with desired properties out a vast number of droplets. The system is therefore particularly well suited for screening methods. For instance microfluidic droplets may be generated that contain microorganisms of genetic variety, wherein a certain morphological phenotype is desired. By simply imaging the microorganisms within the sorter those microorganisms can be selected that meet the specified morphology criteria. Likewise the system can be used for instance for a screening of enzymatic reactions. In this case picoliter droplet may be continuously generated or provided in a pool reservoir that contain variants of enzymes, which yield a fluorescent signal when interacting with a substrate. By detecting said fluorescent signal single microfluidic droplet can be singled out that contain particularly potent variants of the enzyme. A particular advantage of the system however is that it can be used for wide variety of the assays for selecting desired components involved in biological or chemical reactions. Since the sorter relies on the optical signal emanating from the droplet the selection procedure assures a minimal interference with the content of the droplet. In the prior art it was not possible to individually access the content of selected droplets outside of a microfluidic system. This drawback is overcome by the system according to embodiments of the invention in which the sorter is combined with a detector and a collector. Using the system the selected picoliter droplet may transported towards the detector that comprises a detection channel preferably made out of an optical transparent material. Since the detection channel is situated in between a light source and a photodetector the passage of the selected droplet can be detected with high temporal precision. The system is configured such that the relative movement of the collector and the detector may be electronically controlled based on the signal generated at the photodetector. Therefore each picoliter droplet passing through the detection channel can be placed into a separate well. The system is therefore not only capable of selecting droplets with a desired content, but also to extract these droplets from a microfluidic system into wells for instance of a commercially available microtiter plate. The term isolation of a picoliter droplet preferably refers to the combination of these two features. Hence isolating a picoliter droplet preferably refers to the selection of a picoliter droplet within a microfluidic system for a desired property and the subsequent extraction of the selected picoliter droplet from the microfluidic system by depositing it into a well.

An advantage of the system is that for this detection and deposition procedure the droplets may arrive at an arbitrary temporal spacing. A regular spacing of periodically arriving droplets is not necessary. Instead picoliter droplets may be continuously provided to the sorter of the system, while only those droplets that meet the selection criteria are isolated by depositing them into separate wells. Thereby the system allows for particularly efficient screening methods in which reaction components can be optically preselected using the sorter and isolated into separate wells for subsequent analysis and/or a scale up. A particular advantage of the system is that after the isolation step only a part of the content of the droplet can be used for an analysis, while the rest is preserved. This allows for a particular flexible downstream processing of the content of the droplets. For instance using the system microorganisms contained in droplets may be preselected based upon phenotypic criteria and subsequently sequenced. Depending on the genotype the corresponding preserved microorganism can be replicated for a scale-up and further experimentation. This was not possible in the prior art, since the manipulation of picoliter droplets was constrained to microfluidic devices. It was completely surprising that the system according to embodiments of the invention result in a particularly accurate and surprisingly low-error device for transporting and isolating droplets in the picoliter range. The system is further particular well suited to detect individual picoliter oil-in-water compartments that can be present, for example, on a microfluidic chip and automatically deposited them into provided cavities, for example, cavities outside said chip.

The combination of a sorter with a detector and collector, that are movable with respect to each other, allows for single droplet collection of surfactant stabilized emulsions in the picoliter range from a microfluidic system in continuous flow into separate cavities. This new combination for the isolation of picoliter droplets can be applied to variety of processes in which separation of individual samples from many thousands of source samples is required. For example, chemical, biological, and genetic libraries of millions of samples can be transferred into a microfluidic system, analyzed in a high throughout method, and samples with properties of interest can be isolated using the system described here. Potential fields of application are active substance research, clinical tests for drug screening, and industrial applications in the field of molecule optimization.

The term of a "droplet" as used herein refers to an isolated portion of a first fluid surrounded by a second fluid. The first fluid comprises preferably a hydrophilic fluid such as water or an aqueous media or a buffer, which may contain additional components. Such components may be for instance biological components such as cells, proteins or nucleic acids, but may also comprise e.g. chemical reagents. The droplet can constitute an enclosed space in which the components are free to interact. The droplet may therefore serve as a reactor and the first fluid is chosen to constitute a suitable environment for the reaction of said components. The second fluid is herein referred to as a "carrier fluid", which is preferably a hydrophobic fluid. Examples of hydrophobic fluids are hydrocarbons, silicone oils, mineral oils, organic solvent and others. It is preferred that the first fluid and the second fluid are essentially immiscible, which promotes the formation of emulsions. It is particularly preferred that the carrier fluid comprises in addition surfactants, in particular amphiphilic surfactants. A "surfactant" is a substance that reduces the surface tension of a liquid or the interfacial tension between two phases. This advantageously enables and/or promotes the formation of emulsions. Fluorinated surfactants are organic surface-active compounds with an amphiphilic character, consisting of a hydrophilic component (e.g. polyethylene glycol) and a fluorinated hydrophobic component. This allows for a particular stable formation and flow of droplets within the carrier fluid. It is not necessary that the droplet takes a spherical shape, but other shapes may be assumed as well. This may in particular depend on the external environment such as the channels in which the droplets in the carrier fluid are transported.

"Picoliter droplet" refer to droplets with a volume on the picoliter scale. That means a picoliter droplet has a volume in between 1 picoliter and 1000 picoliters preferably in between 10 picoliter and 500 picoliter and most preferably in between 50 picoliter and 300 picoliter. Due to the small volume the picoliter droplets are particularly suited to serve as a reactor for chemical and/or biological reactions.

It is known how picoliter droplets with various chemical and/or biological content may be generated and provided to the system. Microfluidic droplets on the picoliter scale can include, for example, cell suspensions, liposomes, nanocapsules and/or dissolved reagents. The term "dissolved reagents" denotes cell-free systems, proteins, enzymes, biological molecular complexes of non-cellular origin, such as dyes, synthetic antibiotics, nanoparticles, synthetic molecules, complexes, for example, complexes of multiple biological components and/or atomic groups or atoms. "Cell suspensions" are selected from a group including suspensions of prokaryotic cells and/or eukaryotic cells or cell components, respectively. The average person skilled in the art knows that a cell suspension can include one or several types of cells, optionally together with cell components or fragments. It is also preferred that the picoliter droplets contain cell-free systems. These cell-free systems can preferably be used for fatty acid synthesis, DNA replication, RNA synthesis, protein synthesis, or for transcription assays or translation assays, respectively; it is also possible, of course, to perform this reaction in systems which include natural or synthetic cells.

The term "cell culture" or "cell cultures" is used as a cover term for the cell suspensions included in the microfluidic droplets and dissolved reagents. The concept of cell suspension includes preferably natural or synthetic cells, such as lipid vesicles.

The average person skilled in the art knows that the term "dissolved" includes such reagents which may be suspended or emulsified or are present as a solution or as a homogeneous mixture, respectively, in the picoliter droplets.

Advantageously the sorter is configured to allow the passage of picoliter droplets. The "sorter" refers to a device, an apparatus or a system in which the picoliter droplets can be selected and transported to different compartments. The sorter comprises at least one microfluidic chip comprising at least one inlet channel and at least two outlet channels.

Herein the term "microfluidic chip" refers to a device, apparatus or system including at least one fluid channel having a cross-sectional dimension of less than 1 mm preferably less than 500 µm most preferably less than 200 µm and a ratio of length to largest cross-sectional dimension of at least 3:1 preferably at least 5:1 and most preferably at least 10:1. A microfluidic channel as used herein is a channel meeting these criteria. A microfluidic chip with the above dimensions is considered a microfluidic chip configured for the passage of picoliter droplets.

A "channel," as used herein, means a feature on or in an article (substrate) that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel.

The droplets within the carrier fluid are guided towards the inlet channel of the microfluidic chip of the sorter and based upon a selection criteria the droplets are sorted to one of the at least two outlet channels. The transport of the picoliter droplets into the sorter may be achieved by various methods known to a person skilled in the art as for instance by electronically controllable pumps. Herein the flow rate of the carrier fluid and the packing of picoliter droplets flowing in said carrier fluid will determine the number of picoliter droplets that are provided to the sorter within a given time frame. To control at which rate picoliter droplets are flowing into the sorter a spacer may be installed upstream of the sorter. Such a spacer is typically connected to a reservoir of carrier fluid and can pump additional carrier fluid into the channel that leads to the sorter. Thereby the density of picoliter droplets within the carrier fluid may be decreased, which leads to a larger spacing of picoliter droplets and a decreased rate of picoliter droplets flowing into the sorter.

The direction of flow of the carrier fluid transporting the picoliter droplets is preferably used to define relative positions of components of the system.

Therefore the term "upstream" refers to components or units of the system that are situated in the direction opposite to the flow of fluid within the system from a given reference point.

In analogy the term "downstream" refers to components or units of the system that are situated in the direction of the flow of fluid within the system from a given reference point.

In a preferred embodiment the microfluidic chip of the sorter comprises microfluidic channels that form a Y-shaped junction and/or a pair of electrodes configured for a dielectrophoretic sorting of the droplets. This geometry for a microfluidic chip proved to be particularly efficient for a sorting of the droplet. It is preferred that one of the outlet channels of the microfluidic chip is connected to a waste reservoir, while the other outlet channel is connected to the downstream detector. Picoliter droplets that do not meet the selection criteria are guided towards the waste reservoir. It is further preferred that the microfluidic chip is configured such that a guidance of picoliter droplets from the inlet channel to the outlet channel leading to the waste reservoir takes place, when no voltage is applied at the electrodes. Per default the picoliter droplets are therefore guided towards the waste channel. This reduces energetic costs of the sorting device. However if it is determined that a picoliter droplet contains components of a desired property a temporal alternating voltage is applied to the pair of electrodes. This creates a temporal changing electrical field and due to dielectrophoretic forces the picoliter droplets are guided towards the outlet channel that leads to the detector. Advantageously for the dielectrophoretic sorting the picoliter droplets do not need to possess an electrical charge.

It is noted that the transport of the picoliter droplets is in general preferably achieved by the generation of a flow of the carrier fluid. It is therefore preferred that the picoliter droplets are passively dragged with the carrier fluid flow. It is further preferred that the picoliter droplets are actively pushed into the channel by means of pumps. The flow of carrier fluid and additionally the flow of injected droplets into the sorter therefore also determines the carrier fluid flow into the outlet channels of the sorter, whereas the prevailing pressure regime downstream of the sorter affects the fluid flow of every single outlet channel. It is preferred that the majority of carrier fluid is guided towards the waste reservoir. This ensures a reduced fluid flow rate at the detection channel. Moreover in the absence of an electrical field generated at the electrodes the picoliter droplets are advantageously guided towards the waste channel by hydrodynamic focussing. Herein preferably only selected picoliter droplet are moved in a direction deviating from the carrier fluid flow by means of dielectrophoretic forces as described above.

In a preferred embodiment the sorter comprises a second light source and a camera for an optical analysis of the picoliter droplets, whereby the picoliter droplets are sorted based upon an image of a picoliter droplet detected by said camera. It is further preferred that the microfluidic chip is at least partially optically transparent such that the second light source and the second camera can be used to optically observe the content of a picoliter droplet. It is particularly preferred that an optical signal is obtained from the picoliter droplet, while it is situated in the inlet channel upstream of the outlet channels of the sorter. Such an optical signal may be an image of the picoliter droplet detected by said camera. Different imaging techniques are suited in this step including bright field imaging, dark field microscopy, polarized light microscopy and/or fluorescent imaging. The type of imaging as well as the resolution for the imaging of the picoliter droplets will depend on the selection criteria for the components contained in the picoliter droplets. For instance for actinobacteria cultivated in picoliter droplets a 5 fold magnification in bright field illumination has proven useful for the detection of growth of the microorganism. However for other components as for example other microorganisms, cells and/or proteins different imaging techniques and/or parameters may be preferred. A person skilled in the art will be able to tailor the imaging for an optimal selection procedure and know which light source and/or camera to use in this procedure. To this end the microfluidic chip may also be installed into a commercially available microscope with the desired imaging properties. It is further preferred that the image obtained from the picoliter droplet is transmitted to a data processing device such as a computer on which an imaging processing software is installed. The steps of the image analysis will depend on the selection criteria and may include for example filtering steps, contour detection and/or intensity measurements. Examples of an image analysis particularly suited for growth-dependent selection of microorganism cultivated in picoliter droplets are disclosed in Zang et al. Lab Chip, 2013, 13, pp. 3707-3713.

A particular advantage of the system is that the imaging and the image analysis may be performed without the need for additional labels. For instance cells cultivated in droplets may be selected for a high growth rate by selecting the droplets with the highest density of cells. Herein a selection criteria may be the overall measured intensity within the droplet, wherein a low intensity in a bright field image corresponds to a high density of cells. The label free selection procedure allows for a particular flexible usage of the system. Likewise it may however be preferred that the picoliter droplets are selected based upon a fluorescent signal. To this end a fluorescent image visualizing for instance fluorescently labeled proteins within cells cultivated in the picoliter droplets may be obtained. It may however also be preferred to only detect the overall fluorescence intensity from a picoliter droplet. In this case instead of a camera a photodetector may be sufficient.

In a preferred embodiment of the system the sorter comprises a second light source and a second photodetector for an optical analysis of the picoliter droplets, whereby the picoliter droplets are sorted based upon a fluorescent signal of a picoliter droplet detected by said second photodetector. It is further preferred that the microfluidic chip of the sorter is at least partially optically transparent such that the second light source and the second photodetector can be used to optically observe the content of a picoliter droplet. It is particularly preferred that the fluorescent signal is obtained from the picoliter droplet, while it is situated in the inlet channel upstream of the outlet channels of the sorter. For instance picoliter droplets may be provided to the system that contain a population of enzymes which yield a fluorescent signal depending on their reactivity. The most reactive types of enzymes encapsulated in single picoliter droplets may be selected based upon the total fluorescence intensity detected at the second photodetector. Herein a preferred selection criteria may constitute a detected total fluorescence intensity that exceeds a predefined threshold.

A particular advantage of the system is that is not limited to specific optical signals and selection criteria, but can be adapted to a wide range of applications. Once it is determined that a picoliter depicts a content with a desired property it is preferred that a temporal alternating voltage is applied at the pair of electrodes configured for a dielectrophoretic guidance of the selected droplet into the outlet channel leading to the detector. The dielectrophoretic sorting based upon an optical signal is particularly fast and ensures a minimal interference with the content of the picoliter droplet.

Downstream of the sorter the selected picoliter droplets are guided towards the detector. This can be preferably achieved by a tube connection of the outlet channel of the microfluidic chip of the sorter to the detection channel of the detector.

The term "detector" refers to a device, an apparatus or a system that is configured for the transport of droplets on the picoliter scale and is capable of detecting the passage of picoliter droplets. The detector comprises a detection channel with an inner cross-sectional dimension smaller than 150 µm in which the carrier fluid and the picoliter droplets are flowing. The term inner "cross-sectional dimension" refers to the characteristic dimension of the detection channel that is perpendicular to said fluid flow. For instance the detection channel may have an inner surface with a circular shaped cross-section. In this case the inner cross-sectional dimension of the detection channel is equal to the inner diameter of the detection channel. However the detection channel may also have an inner surface with a square shaped cross-section for which the cross-sectional dimension would preferably refer to the length of said square. An inner cross-sectional dimension of the detection channel that is smaller than 150 µm is particularly suited to handle droplets on the picoliter scale. For this dimension the picoliter droplets adapt a shape that substantially fills the inner cross-sectional area of the detection channel. That means that in between the inner wall of the detection channel and the outer boundary of the picoliter droplet only a thin layer of carrier fluid remains. This ensures an efficient transport of picoliter droplets with the flow of the carrier fluid. For a cross-sectional dimension that is substantially larger than 150 µm a transport of picoliter droplets with the carrier fluid may be suboptimal. In this case the carrier fluid may bypass the picoliter droplet in a layer between the inner surface of the detection channel and the outer boundary of the picoliter droplet. It may however also be preferred to have an inner cross-sectional dimension of the detection channel that is larger than 1 µm. Herein the lower boundary for the inner cross-sectional dimension of the detection channel determines the extension of the picoliter droplet in longitudinal direction of the channel, that is the direction of the fluid flow. For dimension that are smaller than 1 µm the picoliter droplet may adopt a longitudinal shape for which the stability of the droplet may be compromised. It is further preferred that the inner cross-sectional dimension of the detection channel is chosen according the desired volume of the picoliter droplet. It is further preferred that the detection channel is optically transparent. To this end it is preferred that the detection channel is made of a material selected from a group comprising glass, silicone and/or polymers such as polystyrene, polyvinyl chloride, polymethyl methacrylate, cyclic olefin copolymer, polycarbonate and/or polydimethylsiloxane.

In a preferred embodiment the detection channel is a capillary preferably a glass capillary. It was surprising that a simple glass capillary is particularly suited for the purpose of the detection channel that is to stably transport picoliter droplets, while enabling a reliable detection. The capillary may however also be made of a different material that preferably transmits light in a wavelength range between 400 and 800 nanometers, that is, is permeable to light with the said wavelengths. The round geometry of a capillary is particularly suited to detect a picoliter drop by detecting a change in the refractive index at the phase boundary of the multiphase system of air and glass on the one side and polymer, oil, and aqueous solution on the other as described above.

In addition to the detection channel the detector according to embodiments of the invention comprises a first light source generating a light beam and a first photodetector, wherein the detection channel is arranged perpendicular to the optical axis of the light beam in between the first light source and the first photodetector. Thereby a passage of a picoliter droplet can be reliably detected by means of indirect measurement of a change in the refraction angle which generates a droplet signal. It is preferred that, when a droplet passes through the detection channel, the outgoing angle of the incident light that enters the detection in orthogonal direction will shift due to spatially and temporally changing phase boundaries and result in a change in light intensity introduced at the first photodetector. The system and method used here preferably represents an indirect optical measurement of the change in a refraction angle, wherein it is preferred that conclusions are drawn from the light intensity recorded at the first photodetector with respect to the change in refraction angle at the phase boundary of the multiphase system between air and glass on the one side and polymer, oil, and aqueous solution on the other side. It is preferred that the light beam whose refraction angle is to be measured indirectly is the light beam from the first light source that is preferably conducted through a multimode optical waveguide to the detection channel. It is preferred that the described recording of the change in refraction angle is preferably called an "indirect measurement" because the changing properties of the light beam are not measured directly but by means of the intensity of the light that arrives at a photodetector.

When a picoliter droplet passes the detection channel the propagation of the light beam, especially the refraction angle due to the phase boundary changes in terms of space and time, which is why a changing light intensity is measured at the first photodetector. In addition, the transmitted light quantity is reduced by total reflection of the incident light that occurs at the phase boundary of the droplets that is water to oil. It is particularly preferred that this leads to a change of light intensity detected at the first photodetector, which converts this change in light intensity into an electrical signal. Said signal that the first photodetector outputs as an electrical signal is preferably called a "droplet signal".

Optical waveguides are preferred for use between the first light source and detection channel and between the detection channel and the first photodetector, which are preferably called glass fibers or fiber optic cables. These are preferably prefabricated optical waveguides, which for example consist of individual fibers made of silica glass and/or plastic. The latter are preferably called polymeric optical fibers. Optical waveguides are typically connected to other optical components, such as light sources or detectors, using plug-in connectors.

Tests have shown that a particularly good light transmission performance can be achieved if multimode optical waveguides are used between the first light source and the detection channel. Depending on its core diameter, an optical waveguide can transmit oscillation modes that are more or less capable of propagation. An oscillation mode in optics preferably corresponds to a normal mode of oscillation in mechanics and preferably represents the energy distribution of a standing wave in multiple spatial directions. A multimode optical waveguide is advantageously suitable for transmitting several thousands of modes, which can preferably be attributed to a large core diameter and corresponds with a heavily structured beam profile. The use of a multimode optical waveguide between the first light source and the detection channel is beneficial mainly to ensure a greater irradiation area into the capillary and therefore a higher yield of the light beams refracted at the capillary, and to ensure that tolerance-related changes in focus can be compensated.

The optical waveguide between the detector and the first photodetector is preferably a single-mode optical waveguide, which is preferably called a monomode optical waveguide. Single-mode fibers are preferably characterized by small core diameters and suitable for propagation of the fundamental mode of oscillation. Its intensity in radial direction is approximately normally distributed, which results in obtaining a particularly uniform beam profile. The average person skilled in the art knows that the number of occurring modes influences signal transmission because the light paths of the individual modes of oscillation differ in length. A particular advantage of using single-mode optical waveguides is that they show very little signal distortion with increasing lengths, which makes them particularly well suitable for signal transmission over long distances.

It is preferred that the single-mode optical waveguide that is preferably disposed between the detection channel and the first photodetector has a preferred core diameter of, for example, 9 µm. It is furthermore preferred that the one of the optical waveguides that is preferably disposed between the first light source and the detection channel is a multimode fiber and has a preferred inner diameter of, for example, 50 µm.

It is preferred that the passage of a picoliter droplet through the light path of the preferably monochromatic light at a preferred wavelength of 400 to 800 nm is detected by the change in refractive index, wherein the change in refractive index is preferably accompanied by a time-variable light intensity that is preferably detected by the first photodetector. It is preferred that the photodetector converts this time-variable signal into an electrical signal, which is called a droplet signal.

It is preferred that the droplet signal is used for controlling the relative movement of the detector with respect to a collector.

Herein the term "collector" refers to a device, apparatus or a system which is configured for the deposition and collection of individual picoliter droplets in separate wells. In particular a collector may also refer to a platform or a device configured for positioning collection wells for the isolated droplets. Herein the term well and collection well is used synonymous and is to be understood in its broad meaning and may refer to any kind of cavity. For instance the collector may comprise a mounting stage onto which a commercially available microtiter plate comprising multiple wells is installed.

For the system according to embodiments of the invention the detector and the collector are configured to move in relation to each other based upon a signal generated at the first photo detector. The signal generated at the first photo detector preferably refers to the droplet signal. As described in detail above the droplet signal is generated upon a passage of a picoliter droplet in the detection channel due to a change of light intensity at the first photodetector. It is preferred that the droplet signal results in a relative movement of the detection channel and the collection unit such the outlet of the detection channel is aligned with the position of a well. The device that allows for the relative movement of the detection channel and the collection unit is preferably referred to as a positioning system. The positioning system therefore refers to equally to systems that allow of a movement of the detection channel and/or the collection unit.

It may be preferred that the collection unit comprises a piezo actuator capable of moving the wells. For instance the wells of the collection unit may be installed on a piezo 3D positioning stage, which allows for a precise electronic motion control. In a piezoelectric material, a change of the electric polarization results in the occurrence of an electric voltage on the material when it is elastically deformed. When using a piezo actuator, the reverse piezo effect is utilized in which a voltage is applied to an actuator material whereby deformation of the material is achieved. Advantageously, it is possible in this way to initiate small movements in the range of 0.1% of the actuator length into any spatial direction depending on the voltage applied and its polarity. Their high accuracy and great dynamics makes piezo actuators particularly well suitable for positioning tasks and for active vibration dampening. An advantage for the use of piezo actuators in the system according to embodiments of the invention is their surprisingly good controllability by means of a voltage to be applied in conjunction with the other electronic components of the system. There are a large amount of commercially available positioning system that either rely on the piezo actuators or other means to control mounting stages in three dimension denoted XYZ. Herein the XY plane preferably denotes the plane in which multiple wells may be positioned on a grid, while the Z-axis preferably denotes the perpendicular direction to the XY plane. Such system are programmable for automated sample transfer, e.g. into microtiter plates. Manufacturers such as cetoni, HiTec Zang, Beckman Robotics, Hudson, Perkin Elemer, Agilent, Tecan, and many others illustrate the technical possibilities of three-dimensional motion sequences. In these systems the X-, Y-, and Z-axes can be installed and controlled separately or simultaneously to perform various motion sequences. It is preferred that the droplet signal triggers a preprogrammed motion sequence on such a stage which results in the alignment of the detection channel with a well of the collector.

It may however also be preferred that the detection channel or preferably the entire detector is attached to a positioning system. In this case the detection unit is moved upon the detection of a droplet, while the collector remains at a fixed position.

A deposition of the detected picoliter droplet into a well may be preferably achieved by surface contacting. Surface contacting means in this case that the detection channel and the collector are aligned in the XYZ-dimensions such that the picoliter droplet in the carrier fluid exiting at the detection channel outlet contacts the bottom of the well and/or a fluid with which the well is filled. The surface contacting therefore implies a passive process that occurs automatically due to the compensation of the interfacial tension.

In a preferred embodiment the system comprises a gas inlet into the detection channel, which is situated below the optical axis of the light beam. It is further preferred that in this preferred embodiment the droplet signal triggers not only an alignment of the detection channel with a well, but in addition a gas pressure is applied at the gas inlet. Through the resulting gas pulse into the detection channel the picoliter droplet can be separated from the continuous stream of the carrier fluid and deposited into the well. The gas inlet together with the necessary means to generate the gas pressure upon a droplet signal is referred herein as a dispenser. The addition of such a dispenser allows for a particular fast and accurate deposition of detected picoliter droplets into a desired well.

It is preferred that the gas inlet of the dispenser and the detection channel are arranged at an acute angle, said angle is variable and its size can be controlled by the dispenser. An acute angle is preferably an angle in the range from 0° to 45°, particularly preferably in the range from 10° to 30°, and most preferably in the range from 20° to 25°.

It is particularly preferred that the passage of a droplet through the capillary in the area of the detection channel is detected due to locally changing phase boundaries over time leading to a change in light intensity introduced into the first photodetector. It is preferred that the first photodetector, as a photoelectronic converter, generates a time-variable electrical signal that is digitally recorded using a transimpedance amplifier and/or analog/digital converter and is preferably used as a control signal for a positioning system and the dispensers simultaneously. It is preferred that the signals are fed into the positioning system using a 15-pole D-SUB signal port however many other electronical ports may be suitable. For example, a software can log this electrical signal, and the axles of a positioning system are preferably triggered when a signal threshold is exceeded, such that a collection vessel is provided at the outlet of the tube conducted through the capillary guider, preferably the capillary. It is preferred that the incoming and detected droplet is either deposited by surface contacting using a defined motion in the XYZ-axis or the deposition is accelerated by a gas pulse triggered at the dispenser. The later can be for example performed by a signal-controlled gas pressure burst pulsed at a time offset from the dispenser, in which a solenoid valve control circuit in combination with TTL signal controlled switching relay and a hardware and/or software controlled signal delay, which is required because of the fluidic flow path, executes adjustable control and, if required, switches the solenoid valve It may be preferred that the gas pressure pulse is produced by a time-variable opening and closing of the solenoid valve controlled by a software-based valve control function. A constant gas flow is applied to the inlet of the solenoid valve which causes a gas flow towards the detection outlet after a signal controlled opening action of the solenoid valve which is interrupted after another control signal by a closing action of the solenoid valve.

In preferred embodiment the system is characterized in that the collector comprises 10 to 10 000 wells preferably 50 to 500 wells, preferably with a volume of 10 nl to 10 ml most preferably 1 µl to 1000 µl. The number of wells together with the specified volumes of the wells allow for the collection of a large amount of picoliter droplets, while maintaining a sufficiently small overall size of the collector for accurate movement control. This may be particularly desired in case a large number of picoliter droplets is to be screened and isolated by the system. It is further preferred that the wells are filled with a fluid that provides favorable conditions for the content of the picoliter droplets. For instance in case the picoliter droplets contain cells and/or enzymes the wells preferably contain a buffer solution favorable for said cells and/or enzymes. Likewise in case the picoliter droplets comprise chemical reagents a suitable buffer is preferably provided within the wells.

It may further be preferred that one of the wells of the collector serves as a waste well. For the time during which no passage of a picoliter droplet is detected the outlet of the detection channel is aligned with said waste well which takes up the outflowing carrier fluid.

In another preferred embodiment the detection channel of the detector is a capillary that is fixed within a capillary guider comprising two connector sockets arranged on the optical axis of the light beam, wherein the first connector is configured to receive a first optical fiber that extends from the first light source and the second connector is configured to receive a second optical fiber that extends towards the first photo detector. Such a capillary guider advantageously ensures an optimal alignment of the optical fibers, the light source, the first photodetector and the detection channel for a detection of picoliter droplets.

It is particularly preferred that the detection channel of the detector is a capillary that is fixed within a capillary guider comprising two connector sockets arranged on the optical axis of the light beam, wherein the first connector is attached to a first optical fiber that extends from the first light source and the second connector is attached to a second optical fiber that extends towards the first photo detector.

The capillary guider is preferably disposed orthogonally to the optical axis of a preferably entering and/or leaving light beam and is concentrically flush with a pipette tip mounting shaft at the outlet on the sensor bottom, wherein said capillary guiding structure guides a capillary with a preferred outer diameter in between 1.6 mm and 300 µm.

For general easier applicability, the geometry of the mounting shaft is preferably designed for the attachment of commercially available pipette tips for volumes from 0.5 to 10 µL. The mounting shaft emulates the one that comes with a commercial pipette. In addition, the range of preferred outer capillary diameters is selected such that standardized capillaries can be applied. In addition to the modular design of the system, this feature makes its immediate application in existing systems easier. In addition to the concentric alignment of capillary and pipette tip, the capillary end preferably terminates somewhat beneath the pipette tip to guide the sheath fluid to the capillary just before the capillary terminates, such that, first, the draining fluid can be reproducibly separated and, second, fluid drops generated at the outlet will not wet the pipette tip and cause cross contamination during a temporal increase in their volume.

The capillary guider comprises preferably an outlet on its bottom side that is concentrically flush with a pipette mounting shaft. This outlet disposed on the bottom side of the capillary guider preferably faces a dispenser. It may further be preferred that the capillary guider is produced in a 3D printing process and results in fixed guidance of the optical waveguide in a surprisingly precise tolerance range. This is a decisive advantage of the preferred embodiment compared to conventional systems described in prior art because the small drop volumes in the picoliter range require a particularly precise alignment of the optical waveguide on the optical axis at a tolerance range of just a few micrometers. Such precise positioning as becomes possible with the capillary guider according to the preferred embodiment is achieved in systems and/or devices described in prior art by pricey micromanipulators or special, complex positioning systems that offer individual adjustment. The use of advanced, highly precise CAD (computer-aided design) technologies allows for a particularly accurate and convenient design. Using a 3D printing process based upon CAD of the capillary guider, the expenditure for a capillary guider according to the preferred embodiment typically does not exceed 20 euros. When using a capillary guider according to the preferred embodiment, the particularly precise adjustment required for picoliter droplets can be achieved surprisingly inexpensively and without additional personnel and time. In particular, a multitude of capillary guiders according to the preferred embodiment can be produced particularly fast and inexpensively using 3D printing methods, wherein any desired three-dimensional geometry can be implemented. Advantageously, such capillary guiders can be produced that include undercuts and could not be produced with conventional mechanical and/or casting processes.

It is particularly preferred that the capillary guider is produced by selective laser sintering (SLS), wherein selective laser sintering preferably is an additive layer process. It is further preferred that polyamide is used as the material for producing the capillary guider according to some embodiments of the invention. The average person skilled in the art knows what other materials can be used for producing a capillary guider according to some embodiments of the invention. Producing the capillary guider in a 3D printing process results in the following structural properties of the capillary guider according to some embodiments of the invention, which make it apparent to an average person skilled in the art that the capillary guider was produced using a 3D method:

Layer-by-layer processing makes layers recognizable in the finished model

Partial melting processes that occur in SLS can easily produce a slightly rough surface Material can have a metallic, ceramic, or plastic character.

In the preferred embodiment of a system comprising a capillary guider, the two connector sockets are preferably disposed next to one another on the optical axis and perpendicular to the capillary guiding structure, wherein a first connector socket is disposed between the capillary and a light source and the capillary and the light source can be connected using a multimode optical waveguide and a second connector socket is disposed between the capillary and a photodetector, and the capillary and the photodetector can be connected using a single-mode optical waveguide.

A capillary guider according to some embodiments of the invention is therefore preferably characterized in that the two opposing connector sockets on the optical axis are disposed such that they are perpendicular to the capillary guiding structure, wherein the single-mode optical waveguide enters the connector socket on the one side via an LC connector and is connected on a modular basis to a light source with a shaft sleeve via an SC connector. It may be further preferred the light source is an indium gallium arsenide light source with a wavelength of preferably 650 nanometers, wherein especially monochromatic light is emitted. It is preferred that the outgoing multimode optical waveguide coupled to the opposite LC connector socket is disposed on one photodetector per SC connector socket. It may be further preferred that the photodetector is a silicon photodetector and that the optical waveguides are configured as LC glass fibers. The shaft sleeve preferably has a diameter of 2.5 mm.

The multimode fiber is preferably equipped like the single-mode fiber with LC and SC-terminating plug-in connectors.

The abbreviation "LC" preferably stands for "local connector", whereas the abbreviation "SC" preferably stands for "subscriber connector". The connector types designated with these abbreviations are the most commonly used connector types in the field of optical plug-in connectors for connecting components of optical systems to optical waveguides. This results in good availability of the connector types.

A LC connector is particular advantageous because its geometry is suited for a higher connection density compared to other widely common connector configurations. This also means that the capillary guider can be dimensioned smaller. The SC assembly is a larger predecessor of the LC connector with a receiver for 2.5 mm ferrules. Such ferrules are standard attachments to light sources for contacting with LC connectors, but also with widely common standard connectors in the ST format. In general, a combination of optical fibers prefabricated for LC and SC/ST are common. The contacting between the light source and the capillary guider is not limited to a connector type as long as light conduction from the light source to the capillary with a respective modular receiver and light conduction from the capillary to the detector are ensured.

Application tests have shown that the use of an indium gallium arsenide light source is particularly advantageous because its compact design facilitates fast, cost-effective and space-saving installation and operation at performance parameters similar to those of large laser modules.

In another preferred embodiment, capillary guider is configured to receive the gas inlet of the dispenser. It is further preferred in this embodiment that the dispenser includes a two-way solenoid valve that is connected to the gas inlet, a switching relay connected to said two-way solenoid valve, a Schmitt trigger, a signal delay, and a pipette tip that interrupts the gas flow, wherein said dispenser is connected via said gas inlet and a hose feed to the capillary guider, wherein said hose feed is connected to the two-way solenoid valve.

It is preferred that the two-way solenoid valve is disposed in a hose feed, wherein said valve can be closed or open. This preferably allows or prevents the supply of a gas to the capillary of the system according to some embodiments of the invention. The solenoid valve is preferably controllable. It is preferred that the gas supply is pressure regulated and a switching relay, which is also connected to the solenoid valve, can be controlled by a TTL signal, wherein said signal preferably is the droplet signal which is generated when a picoliter droplet passes through the capillary of the system according to some embodiments of the invention in the area of the capillary guider and said droplet passage is detected by the photodetector. The signal delay can preferably be controlled by a hardware and/or software.

According to this embodiment, the dispenser for separating the continuous fluid stream of picoliter droplets consists of a two-way solenoid valve, a switching circuit that can be controlled by a TTL signal and is connected to the solenoid valve, a Schmitt trigger, a hardware and/or software controlled signal delay, and a pipette tip that terminates the gas flow, wherein said dispenser is connected to the capillary guider via said gas inlet via a hose feed, which itself is connected to the switchable solenoid valve which is controlled by the droplet signal, which solenoid valve is connected to a pressure regulated gas supply.

In another preferred embodiment of some embodiments of the invention, the droplet signal can be converted into a digital signal using the Schmitt trigger. This digital signal can advantageously be used to control the switching relay and the solenoid valve.

A Schmitt trigger is an electronic comparator circuit in which the on or off thresholds advantageously do not coincide but are offset from one another by a defined voltage. The Schmitt trigger can therefore be used within the system according to some embodiments of the invention to generate binary signals, which therefore can be translated for the switching relay and the solenoid valve, or to generate unique switching states from an analog input signal curve. The Schmitt trigger preferably works as a comparator of two analog voltages, which unlike a mere comparator has different on and off thresholds that are set apart by a hysteresis value.

In addition to the advantages mentioned above, the use of a Schmitt trigger has the positive characteristic of compensating analog noise and potential false positive signals that may occur in the experiment (oscillations in the system due to the movement of the positioning system and therefore potential movements of the capillary and optic fibers) within a certain range. This range describes all false positive signals whose strength does not exceed the reference voltage.

It is further preferred that the system according to the preferred embodiment includes a positioning system for controlling the collection of the picoliter droplets, wherein said positioning system consists of a separately addressable XY plane and a Z-axis, an attachment on the XY-axis for at least one collection well, a mounting plate fastened to the Z-axis, and a 15-pin D-SUB signal socket. It is further preferred that the capillary guider is locked onto the mounting plate located in the Z-axis. In addition, it is preferred that axial triggering of the positioning system is performed by external analog and/or digital signals from the capillary guider fed in via the 15-pin D-SUB signal socket.

In another preferred embodiment in which the system comprises a capillary guidance, to a fastening device of the capillary guider is fastened with fastening means to a Z-axis of a positioning system. It is preferred that the fastening device is for example a screw clip and that the fastening means are for example formed by M5 screws. Advantageously, the fastening device allows particularly secure and in particular detachable fastening of the capillary guider to a positioning system, such that the individual components of the system can be disassembled and/or assembled, wherein in particular the replacement of individual components and/or their maintenance, cleaning and/or repair can be performed particularly easily. The reversible design of the fastening of the capillary guider to the positioning system of the system ensures particularly high flexibility of the assembly of the individual components. Such a preferred embodiment of the system can preferably referred to as a modular system that can particularly easily and flexibly be adapted to changed conditions of the test arrangement and/or the results to be achieved.

It was completely surprising that in this preferred embodiment a system modular design could be provided that can be reversibly assembled and disassembled. This is an advantage of the preferred embodiment, above all, for cost and flexibility reasons, because individual components of the system according to this preferred embodiment can be used as desired in other test arrangements, which can reduce acquisition costs.

Some embodiments of the invention further relate to a method for isolating picoliter droplets comprising
1) providing a system comprising
   a) a sorter comprising a microfluidic chip configured for the passage of picoliter droplets and their selection based upon an optical signal obtained from the picoliter droplets,
   b) a detector comprising a detection channel with an inner cross-sectional dimension smaller than 150 µm, a first light source generating a light beam and a first photodetector, wherein the detection channel is arranged perpendicular to the optical axis of the light beam in between the first light source and the first photodetector, and
   c) a collector comprising multiple wells,
   wherein the detector and the collector are configured to move in relation to each other based upon a signal generated at the first photodetector,
2) transporting a picoliter droplet in a carrier fluid towards the sorter,
3) selecting a picoliter droplet within the microfluidic chip based upon an optical signal obtained from said picoliter droplet
4) transporting the selected picoliter droplet towards the detection channel
5) detecting the passage of a selected picoliter droplet through the light beam in the detection channel due to a change of light intensity measured at the first photodetector
6) triggering a movement of the detection channel and/or the vcollector when a passage of a picoliter droplet has been detected in step 5), and
7) depositing the picoliter droplet into a well.

Technical features that have been disclosed for the system according to some embodiments of the invention preferably also apply for the method according to embodiments of the invention. A person skilled in the art will therefore recognize that preferred features of the system according to some embodiments of the invention can be advantageously used as well in the context of the method according to embodiments of the invention. For instance, in the method according to embodiments of the invention, a picoliter droplet is selected within the microfluidic chip of a sorter based upon an optical signal. Preferred embodiments of the sorter described for the system such as a sorter that comprises a second light source, and a camera for an optical analysis of the picoliter droplets, whereby the picoliter droplets are sorted based upon an image of a picoliter droplet detected by said camera, are also preferably provided for the use of the method according to some embodiments of the invention. This applies to the components of preferred embodiments of the system such as for the example above a light source and a camera as well as to the disclosed functional relationships of these components. For the example above a disclosed functional relationship of the system is e.g. that the light source and the camera are used to obtain an optical signal preferably an image of the picoliter droplets. Thus a person skilled in the art recognizes that a preferred step of the method according to some embodiments of the invention may be that the selection in step 3) is based upon an image obtained from the picoliter droplets. It is therefore particularly preferred that the method according to some embodiments of the invention uses a system according to the independent claim and preferred embodiments of said system. Moreover, surprising technical effects disclosed for features of the system can be advantageously exploited in the method according to some embodiments of the invention.

The method according to some embodiments of the invention is surprisingly efficient to isolate individual microfluidic droplets on the picoliter scale for subsequent analysis and/or a scale up of the content of the droplet. The selection of the microfluidic droplets using the sorter advantageously enables to select one single picoliter droplet with desired properties out a vast number of droplets. The selection procedure is preferably carried out using in a microfluidic device, which as described for the system is capable of selecting and sorting picoliter droplets based upon an optical signal that serves as a selection criteria. A "selection criteria" preferably refers to a desired property of content of the picoliter droplet, which is detected by optimal means. For instance it may be desired to isolate cells cultivated in picoliter droplets using the method that possess a certain enzyme that is labelled with a fluorescent marker. Therefore the optical signal in step 3) of the method may refer to the measured fluorescent intensity emanating from the picoliter droplet. The selection criteria may in this case be that the detected fluorescence intensity obtained from a picoliter droplet needs to exceed a predefined threshold. Picoliter droplets that meet the selection criteria are selected to be transported to the detection channel. According to the method of some embodiments of the invention these selected picoliter droplets may be subsequently dispositied into separate wells. The extraction of selected picoliter droplets into wells has not been possible with methods of the prior art. As outlined for the system such an isolation of desired picoliter droplet may be particularly advantageous for example for the screening of clinical drugs, biological research involving the screening of cells and/or organisms or industrial applications in the field of molecule optimization.

In a preferred embodiment the method is characterized in that the picoliter droplets comprises an aqueous buffer and a biological material preferably selected from a group consisting of eukaryotic cells, prokaryotic cells, plant cells, viruses, proteins and/or nucleic acids. Herein a biological material is preferably understood broadly referring to any kind of living matter or components that take part of a living matter and can comprise components ranging in scale from molecules, cells to entire organisms. It is preferred that the biological material is suitable for a scale up which means it can be replicated. It was surprising that the method according to embodiments of the invention is particular suited for screening methods that involve biological materials such as cells, microorganisms or proteins. The picoliter droplets comprising a suitable aqueous buffer constitute a small reactive volume in which the biological material can be maintained at physiological conditions. Moreover reactions between components of the biological materials for instance reactions between an enzyme and a substrate can take place with a particular high efficiency due to the small volume of the picoliter droplet. These advantages of the picoliter-droplet technology as microreactors for biological materials are exploited by the method according to embodiments of the invention. The method according to embodiments of the invention not only allows for a selection of biological material with a desired property based upon an optical signal, but also for a collection of a selected picoliter droplet into an individual well. Due to this isolation procedure the biological material comprising for instance cells are accessible outside of a microfluidic device for subsequent analysis and/or further biotechnological processing.

In a preferred embodiment of the method part of the content of the well into which the picoliter droplet has been deposited in step 6) is extracted for a subsequent analysis and/or a scale-up of the content of the picoliter droplet by replicating a biological material. For instance a part of a selected population of cells, may be extracted from the well for an analysis, while the remaining part is replicated for further use. The preferred method allows therefore for a particular flexible screening of biological materials that involve a preselection based upon an optical signal and may include a variety of subsequent analysis steps as the content is accessible outside a microfluidic system.

In a preferred embodiment the method is characterized in that in step 3) a fluorescent and/or a non-fluoresent image of the picoliter droplet is captured and processed for the sorting of the picoliter droplets. The capturing of an image of the picoliter droplet allows for a quantification of properties of the content of the picoliter droplet. Herein the optical selection method is fast, non-invasive and can be adapted to a variety of applications. For instance it may be desired to find new bacterial mutants for higher biomass yields. To this end a population of mutagenized bacteria may be cultivated in picoliter droplets and provided for the preferred method. By capturing an image of each picoliter droplet in the sorter it is advantageously possible to analyze the growth of the bacteria. Using subsequent processing to analyze the image, picoliter droplets containing bacteria that depict a predefined deviation in their growth yield may be sorted to the detector and subsequently deposited into wells. This constitutes a fast optical preselection of bacteria based upon a morphological criteria. After the deposition into a collection well genotyping may be used to identify the mutation and establish a library of the desired bacterial strains. The possibilities for the sorting of picoliter based upon an acquired image are vast. The preferred embodiment of the method is therefore characterized by a high flexibility and suited for a number of applications.

In a further preferred embodiment the method is characterized in that in step 3) the emission of a fluorescent signal originating from a picoliter droplet is measured and is used as a selection criteria for the sorting of the picoliter droplet. Fluorescence as a selection criteria enables a variety of applications of the method for instance in medical screening, biological research or chemistry. For instance genetically modified cells may be cultivated that express a certain type of fluorescently labelled protein. By detecting the fluorescence signal of the picoliter droplet the preferred method allows to isolate cells with a particular high expression of said protein. Likewise cells may be cultivated in picoliter droplets together with fluorescently labelled anti-bodies against e.g. a specific membrane protein. By detecting a fluorescent image of the cells contained in the droplet, picoliter droplets containing cells presenting these membrane proteins may be easily distinguished and isolated for further processing. In comparison to existing methods for a fluorescence based screening involving a FACS system an important advantage of the method presented herein is that it allows to isolate cells not only based upon a fluorescent signal that emanates from the cells, but also based upon a fluorescent signal that emanates from the environment with which the cells interact. Thereby it is for instance possible to use the method for a screening of cells or organisms for the expression of secreted molecules. In contrast to a FACS system fluorescently labelled molecules that are secreted by a cell or an organism within the picoliter droplet may be detected by the method and serve as a selection criteria. Moreover the method is particularly well suited for assays involving cell-free system. For instance enzymatic activity may be quantified based upon a fluorescent signal and the method may be exploited for a fast and efficient screening for enzymes with an elevated activity.

In a preferred embodiment the method is characterized in that more than 10 preferably more than 100 and most preferably more than 1000 picoliter droplets per second are sorted. These rates of picoliter droplets entering the sorter of the system are particular advantageous for screening a large pool of picoliter droplets. For instance a pool comprising 1 million picoliter droplets may be sorted with a preferred rate of 100 picoliter droplets per second in less than 3 hours.

Advantageously with the method according to embodiments of the invention not all picoliter droplets that enter the sorter are deposited into a collection well. Instead due to the novel combination of a sorter, a detector and collector according to the invention only those picoliter droplets that are selected are subsequently extracted from the microfluidic system and deposited into wells. It is particularly advantageous that the method does not require a periodic deposition of picoliter droplets. Instead the selected picoliter droplet may be deposited at arbitrary, irregular intervals. The method can therefore advantageously adapt to the occurrence of the picoliter droplet with the desired content within the pool that is to be screened. Furthermore using the preferred method the capacity of the collector is optimally used, since it collects only those picoliter droplets with a desired content as estimated by a selection in the sorter.

In another preferred embodiment the method is used to isolate droplets comprising a clonal population of cells in a culture medium. As described above the method according to embodiments of the invention is particularly suited for isolating picoliter droplets from a large pool. It is preferably possible that the large pool of picoliter droplets is generated such that initially each droplet comprises one cell. By cultivating the picoliter droplets the cells may replicate to yield clonal population of cells within each picoliter droplet. Due to the capability of the method to sort and deposit selected picoliter droplets fast and efficient, the preferred method is particularly suited for a high-throughput clonal analysis of a population of cells.

In another preferred embodiment the method is characterized in that the detection of a picoliter droplet in step 5) triggers a streaming of a gas into the detection channel via the gas inlet in order to dispense said picoliter droplet. The pulse of gas in this preferred embodiment of the method assists the deposition of the picoliter droplets, since the gas stream efficiently separates the picoliter droplet from the continuous stream of carrier fluid. With this preferred method the deposition of picoliter droplets can be carried out particularly fast and accurate.

Figure 1:
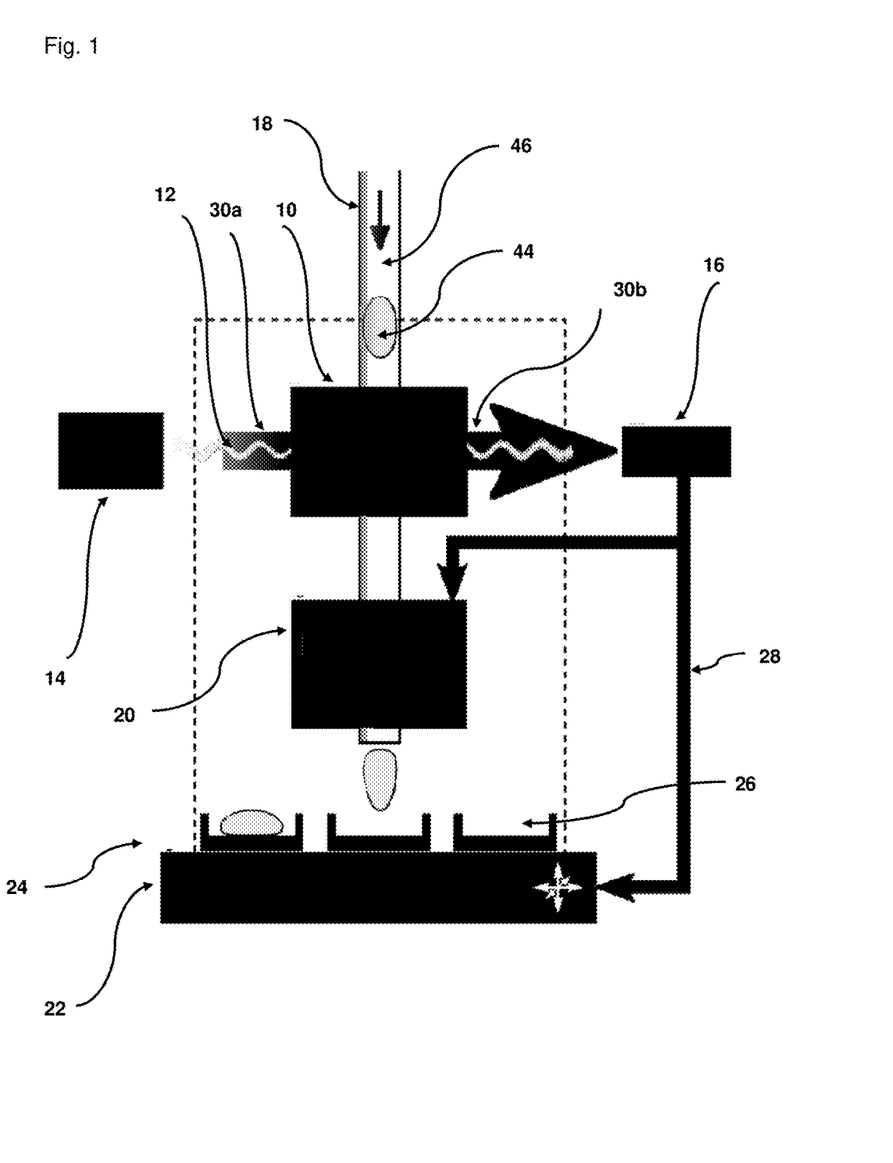
FIG. 1 Schematic view of a preferred embodiment of a part of the system for isolating an individual picoliter droplet.

FIG. 1 shows a preferred embodiment for a part of the system for isolating an individual picoliter droplet. A carrier fluid (46) which contains, for example, biological material is disposed in a capillary (18). A single picoliter droplet (44) is to be separated from this carrier fluid (46), such that said droplet can be further analyzed after passing through the system according to embodiments of the invention. The carrier fluid (46) is conducted in a capillary (18) through a capillary guider (10), and optical waveguides (30) are disposed perpendicular to said capillary (18) which is permeable to visible light. Monochromatic light from a first light source (14) is conducted through said optical waveguides (30), which are, for example, formed by optical fibers and/or glass fibers, wherein the light source (14) is for example formed by a light emitting diode (LED) or an indium gallium arsenide light source (InGaAs), wherein the emitted light (12) preferably has a wavelength of 650 nanometers. The monochromatic light (12) emitted from the light source (14) crosses the light-permeable capillary (18) in which the carrier fluid (46) and the picoliter droplet (44) is disposed.

If a single picoliter droplet (44), which can preferably be unlabeled and in particular does not need to be provided with a fluorescence marker, enters the area of the capillary guider (10) inside the capillary (18) and passes through the same, the optical properties of the monochromatic light (12) will change. In particular, the phase boundaries change in the multiphase system of air and gas on the one side and polymer, oil, and aqueous solution on the other side. Therefore the angle at which the light (12) leaving the capillary (18) exits the capillary (18) changes as well. The first photodetector (16), which can for example be designed as a photodiode (34), detects a changed light intensity due to the changed angle, which the photodetector (16) in its capacity as a photoelectronic converter then converts into a time-variable electrical signal (28). The picoliter droplets (44) are fed to the capillary guider (10) via polymer tube connections, which preferably consist of PTFE, FEP, or PFA and preferably have an outer diameter of 1.6 mm. The picoliter droplets (44) are transferred from the tube connection into the transparent capillary (18) using an adapter (not shown). Monochromatic light (12) from the light source (14) is supplied using optical waveguides (30), wherein said optical waveguide (30) that extends from the light source (14) to the capillary guider (10) is a multimode glass fiber cable (30a) with click/plug-in connections (standard SC-type optical connectors). The optical waveguide (30b) with which the changed light (12) is optionally guided from the capillary guider (10) to the photodetector (16), preferably is a monomode glass fiber cable (30b) with a click/plug-in connection on the capillary guider (10) (standard LC-type optical connector) and a standard SC-type optical connector at the first photodetector (16). The incoming and outgoing optical waveguides (30a and 30b) can preferably be positioned on the left or on the right-hand side of the capillary guider (10).

The first photodetector (16) conducts the electrical signal (28) caused by the passage of the picoliter droplet (44) through the capillary guider (10) on to the dispenser (20) and the positioning stage (22) of the collector (24). Due to the electrical signal a movement of the positioning stage (22) is triggered that leads to the alignment of a collection well (26) of the collector with the outlet of the capillary (18). The picoliter droplet (44) may be deposited by surface contacting. To this end the positioning stage (22) is moved in the Z-direction such that the outlet of the capillary is brought close to the collection well (26). The deposition of the picoliter droplet (44) preferably takes place when the picoliter droplet (44) reaches the end of the capillary (18).

The deposition of the picoliter droplet may however also be assisted by a dispenser (20). In this case the incoming picoliter droplet (44) is dispensed by a gas pressure burst that is generated due to the electrical signal (28) caused by the passage of a droplet through the capillary guider (10), which also results in fast dispension of the picoliter droplet (44). This gas pressure burst is introduced into the capillary (18) by a gas supply or gas feeding line (36).

Figure 2:
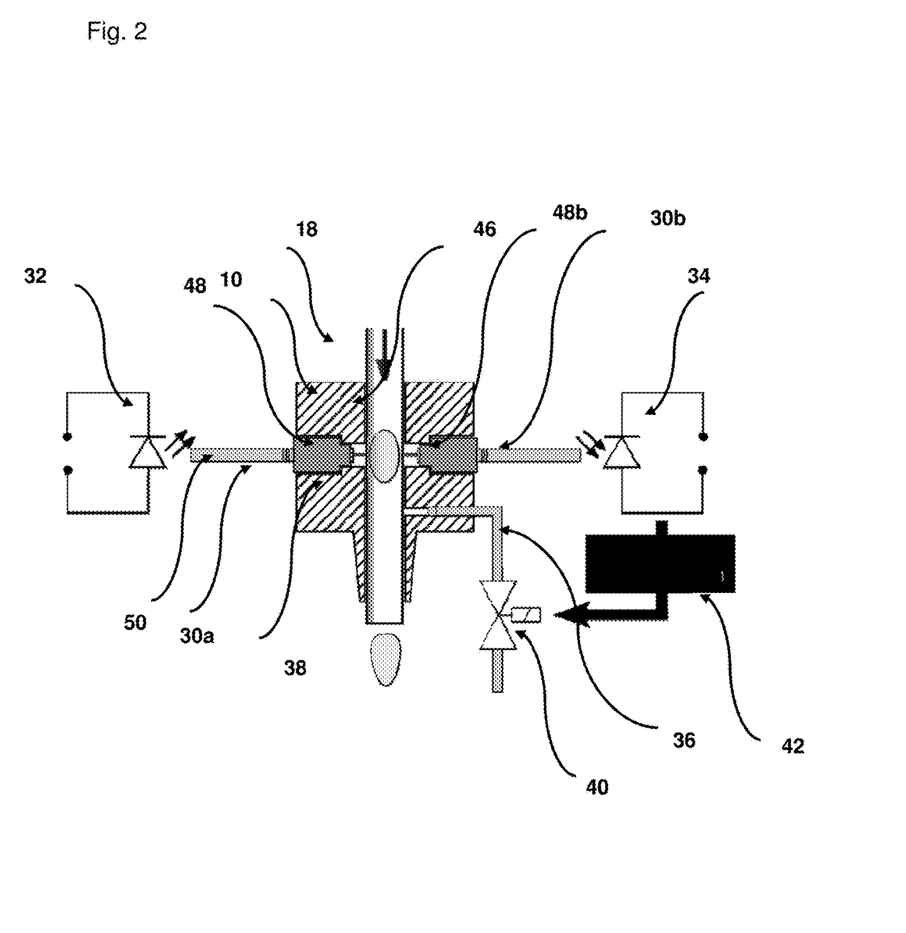
FIG. 2 Cross section depicting a preferred embodiment of a capillary guider with a disperser coupled to it.

This is shown in FIG. 2 which gives a cross-sectional view of a preferred embodiment of the capillary guider (10) with a dispenser (20) coupled to it. The gas supply is regulated in the preferred embodiment of the invention shown using a two-way solenoid valve (40), which is controlled by means of the so-called droplet signal (28). For this purpose, a switching relay is operated after actuation by a TTL signal and a signal delay which is required due to the fluidic flow path and can be controlled by hardware and/or software.

As shown in FIG. 1 the capillary guider (10) is preferably fastened using a fastening device, such as a screw clip, to a Z-axis of the positioning stage (22), wherein the fastening can be implemented using fastening means, such as M5 screws. The electrical signal (28) generated by the photodetector (16) and also called droplet signal is fed via a 15-pin D-SUB signal port into the positioning stage (22). A software logs and triggers the axles of the positioning stage (22) when a signal threshold is exceeded, such that a collection vessel (26) for receiving the arriving picoliter droplet (44) can be provided to the capillary (18) guided by a capillary guiding structure (38) of the capillary guider (10).

The gas feeding line (36) into the capillary for an gas pressure assisted dispensing of the detected picoliter droplet (44) is a tube connection attached to the side of the capillary guider (10). Gas can be conducted to the outlet of the tube due to an exchangeable attachable pipette tip (not shown) for which there is a mounting shaft on the bottom side of the capillary guider (10). The dispensed picoliter droplet (44), which for example contains biological material as an analyte, can be used for further analyses after passing through the system according to embodiments of the invention and completing the method according to other embodiments of the invention.

FIG. 2 shows a preferred embodiment in which the first light source (14) is formed by a light emitting diode (LED) (32). The first photodetector (16) is formed by a photodiode (34), preferably a silicon photodiode. FIG. 2 shows a carrier fluid (46) containing picoliter droplets (44) in a light-permeable capillary (18). Optical waveguides (30a and 30b) connect the LED (32) to the capillary (18) extending through the capillary guider (10) and forming a right angle with the optical waveguide (30). The optical waveguide (30a), which is preferably formed by a multimode fiber, is connected to the capillary guider (10) using a connector socket (48a). After passing through the capillary (18) filled with carrier fluid (46), the light (12) is conducted by another optical waveguide (30b) to the photodiode (34), wherein the connection between the optical waveguide (30b) and the capillary guider (10) is made by a second connector socket (48b). The optical axis (50) of the light beam (12) extends centrally within the optical waveguides (30). The capillary guider (10) includes a guide or guiding structure (38) and a vertical through hole (not shown) which ensures fixation of the capillary (18) and at the same time ensures its positioning in the area of the light beam (12).

The component designated with the reference symbol 42 includes the system components for processing and converting the droplet signal (28), for example, into a digital signal with which the dispenser (20) and the positioning stage (22) are controlled. In particular, the converted droplet signal (28) is used to control the axles of the movable positioning stage and the two-way solenoid valve (40) which allows gas being fed (36) into the capillary (18) to separate individual picoliter droplets (44) from the carrier fluid (46).

Figure 3:
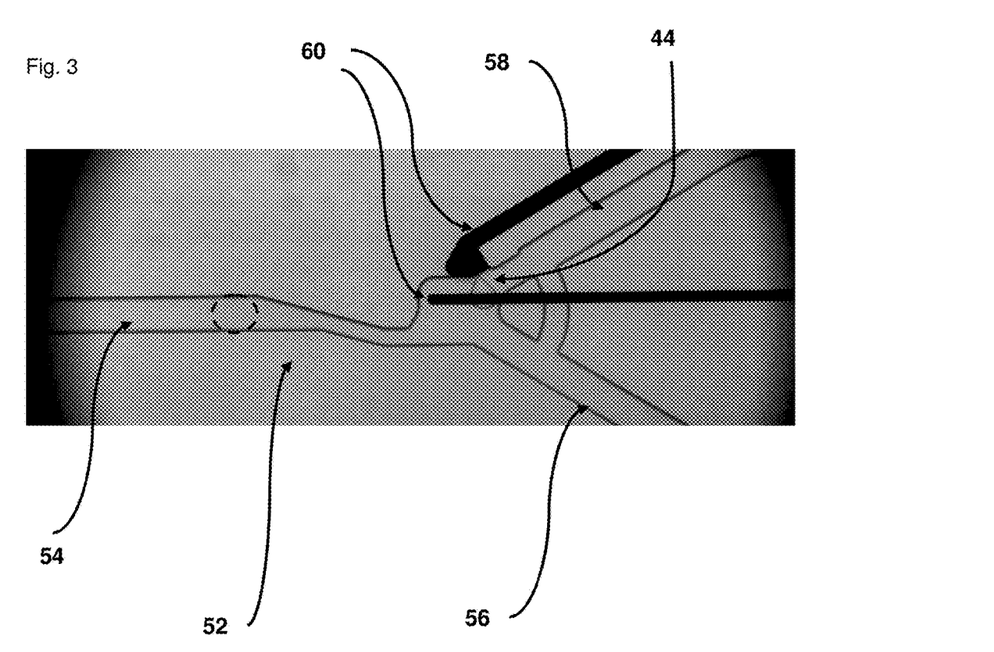
FIG. 3 Image of a preferred embodiment of a sorter depicting a Y-shaped microfluidic chip and a pair of electrodes configured for the dielectrophoretic sorting of the picoliter droplets.

FIG. 3 shows an image of a preferred embodiment of a sorter depicting a Y-shaped microfluidic chip (52) and a pair of electrodes (60) configured for the dielectrophoretic sorting of the picoliter droplets (44). The picoliter droplets enter the microfluidic chip (52) of the sorter at the inlet channel (54). The picoliter droplets are transported by the general flow of the carrier fluid, which is not visible in the image. When no voltage is applied at the pair of electrodes (60) the picoliter droplets are guided into the outlet channel (56) which leads to a waste reservoir. However if a picoliter droplet (44) is selected a voltage is applied at the pair of electrodes (60) generating an electrical field that due to the resulting dielectrophoretic forces directs the picoliter droplet (44) into the outlet channel (58) which leads to the detector. The visible picoliter droplet (44) has just been sorted towards the outlet channel (58) in the depicted image. To determine which picoliter droplets are to be selected and sorted towards the detector an image of the picoliter droplet is obtained in a region indicated by a dashed circle upstream of the junction of the outlet channels (56,58). The region, where an optical signal of the picoliter droplet is obtained may however vary and is preferably adjusted regarding to the geometry of the microfluidic chip as well as the type of sorting. For instance for an image based analytical sorting the region for capturing the image will be chosen sufficiently upstream of the junction of the outlet channels to allow the for sufficient computation time. The position of the region may therefore also depend on the image analysis algorithm as well as the computational power of the data processing machine.

Figure 4:
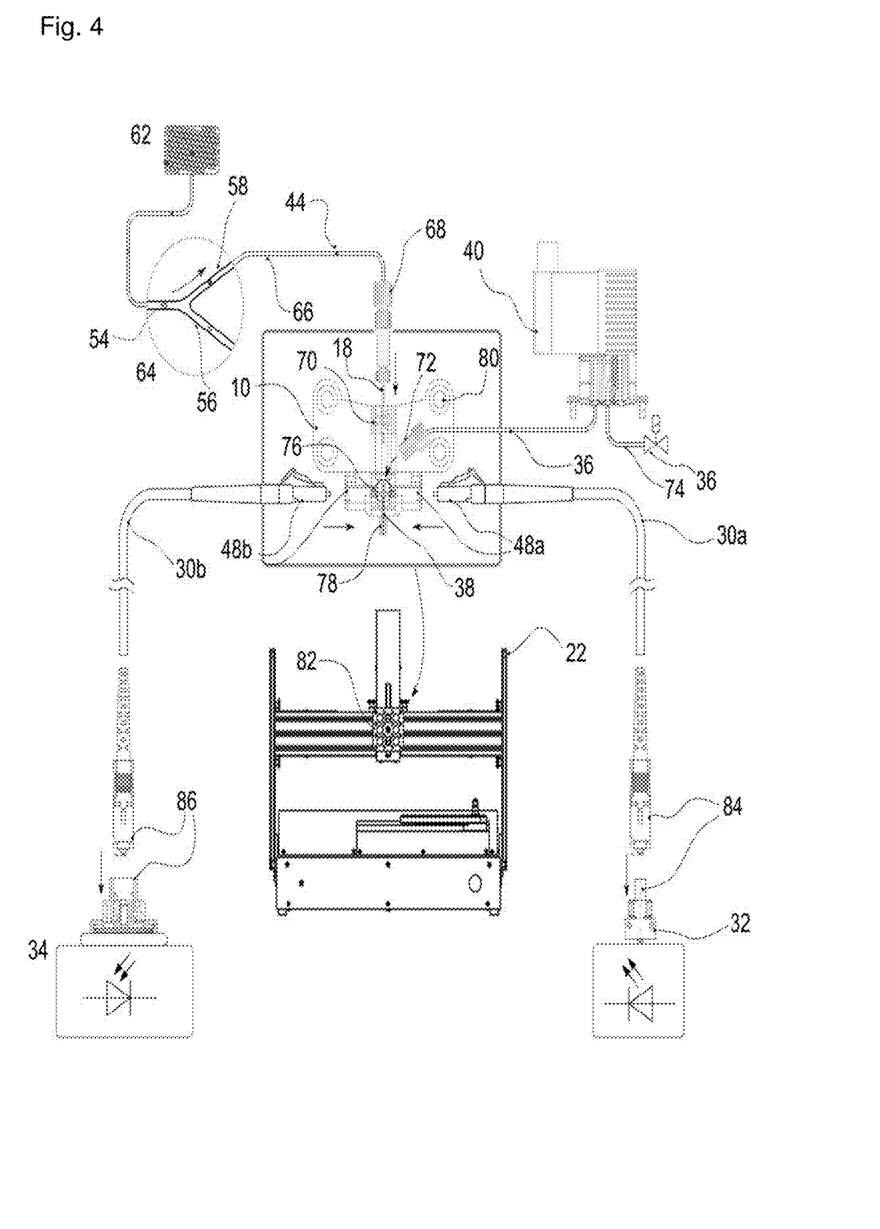
FIG. 4 Schematic representation of a preferred embodiment of the system.

FIG. 4 shows an image of a preferred embodiment of the system. Picoliter droplets from a droplet pool (60) are guided towards the inlet channel (54) of the sorter (64). Within the microfluidic chip of the sorter (64) selected picoliter droplets (44) are guided to the outlet channel (58), which transports the picoliter droplets (44) to the detector, while unselected picoliter droplets (44) are guided into an outlet channel (56), which leads to a waste reservoir (not shown). The depicted detector comprises a capillary guider (10) in which the detection channel is constituted by a glass capillary (18). When a selected picoliter droplet (44) in the capillary passes the light beam generated by the LED (32), the photodiode (34) detects a change in light intensity. In this case the positioning stage (22) of the collector is moved such that a pipette tip (78) at the outlet of the capillary (18) aligns with a well (not shown). The subsequent deposition of the picoliter droplet into the well is assisted by a dispenser, which triggers a pulsed stream of gas into the capillary (18) via an electronically controlled two-way solenoid valve (40).

Figure 5:
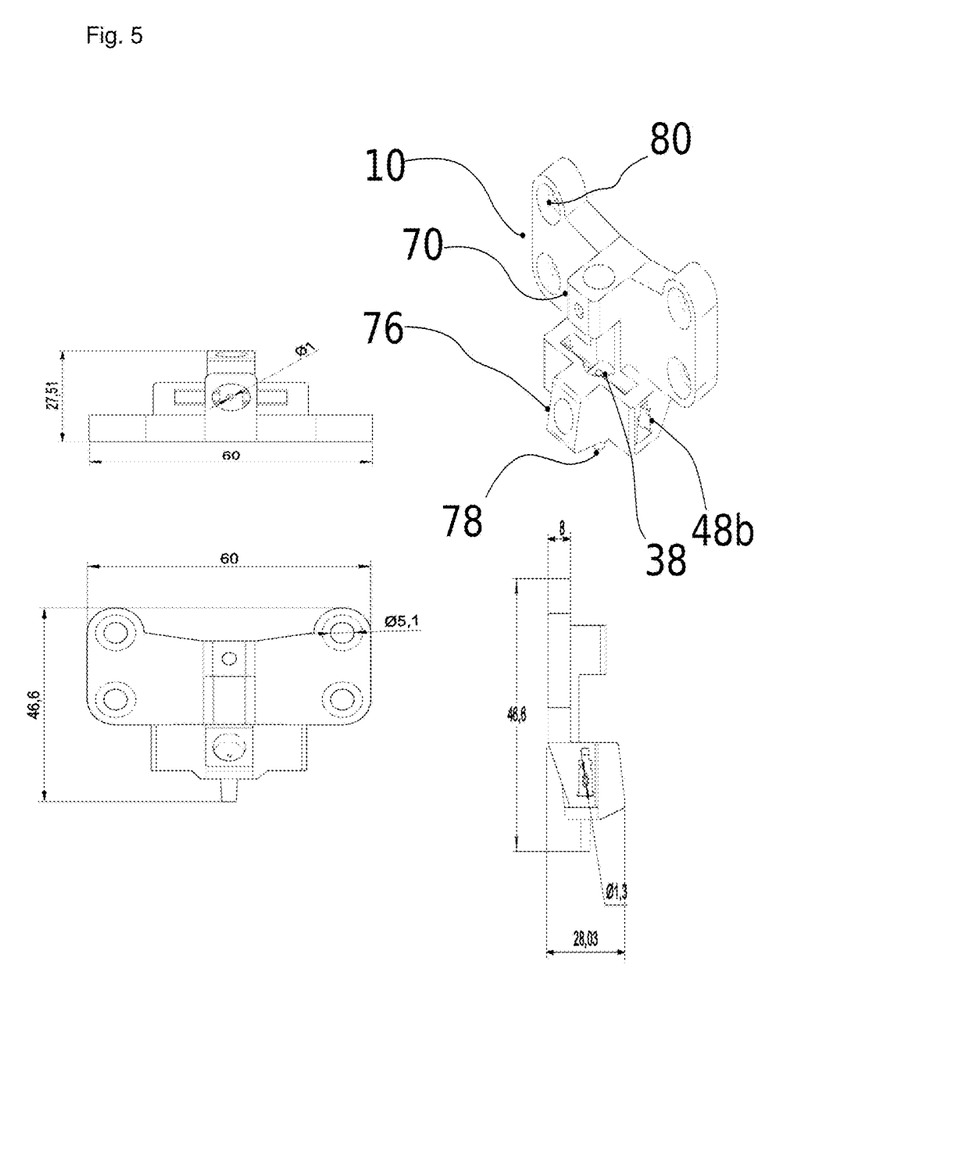
FIG. 5 Schematic representation of a preferred embodiment of the capillary unit.

FIG. 5 is a schematic presentation of the capillary (10) showing four views. On the upper right a three dimensional overview is depicted, which complemented by three corresponding sectional views of the capillary (10).

It should be understood that various alternatives to the embodiments of the invention described herein may be employed. It is intended that the claims define the scope and that the method and apparatus within the scope of these claims and their equivalents be covered thereby.

LIST OF REFERENCE SYMBOLS

10 Capillary guider
12 Light
14 First light source
16 First photodetector
18 Capillary
20 Dispenser
22 Positioning stage
24 Collector
26 Collection well
28 Electrical signal
30 Optical waveguide
  30a: Multimode optical waveguide
  30b: Single-mode optical waveguide
32 Light emitting diode (LED), first light source
34 Photodiode as a first photodetector
36 Gas supply or Gas feeding line
38 Guiding structure
40 Two-way solenoid valve
42 Signal transformation
44 Picoliter droplet
46 Carrier fluid
38 Connector sockets
  48a first connector socket
  48b second connector socket
50 Optical axis of the optical waveguides
52 Microfluidic chip of the sorter
54 inlet channel of the microfluidic chip
56 outlet channel of the microfluidic chip towards a waste reservoir
58 outlet channel of the microfluidic chip towards the detector
60 pair of electrodes configured for the dielectrophoretic sorting of picoliter droplets
62 Droplet pool
64 Sorter
66 Connecting polymer tubing from the microfluidic chip to the capillary/detector
68 Polymer tubing to capillary adapter
70 Capillary adapter fixation
72 Screw connector for pressure
74 Pressure supply pipe to solenoid valve
76 Pressure inlet receptacle
78 Pipette tip
80 Fixation Holes for M5 screws
82 Plate fixed on z-axis
84 LC-Connector
86 LC-Connector/plug-in

What is claimed is:

1. A system for isolating picoliter droplets comprising:
   a) a sorter comprising a microfluidic chip configured for the passage of picoliter droplets and their selection based upon an optical signal obtained from the picoliter droplets, wherein the sorter comprises a first light source and a camera or a first photodetector such that the picoliter droplets are sorted based upon the optical signal obtained by the camera or the first photodetector,
   b) a detector comprising a detection channel with an inner cross-sectional dimension smaller than 150 µm, a second light source generating a light beam and a second photodetector, wherein the detection channel is arranged perpendicular to the optical axis of the light beam in between the second light source and the second photodetector, such that the passage of a picoliter droplet is detected by a change of the refraction angle of said light beam upon which the second photodetector outputs a signal, and
   c) a collector comprising multiple wells,
   wherein the detector and the collector are configured to move in relation to each other based upon the signal generated at the second photodetector, and wherein detection of the passage of the picoliter droplet results in a relative movement of the detector and the collector, such that the picoliter droplet is isolated by depositing it into one of the multiple wells.

2. The system according to claim 1, wherein the microfluidic chip comprises microfluidic channels that form a Y-shaped junction and/or a pair of electrodes configured for a dielectrophoretic sorting of the droplets.

3. The system according to claim 1, wherein the picoliter droplets are sorted based upon an analysis of an image of a picoliter droplet detected by the camera.

4. The system according to claim 1, wherein the picoliter droplets, whereby the picoliter droplets are sorted based upon a fluorescent signal of a picoliter droplet detected by the first photodetector.

5. The system according to claim 1, wherein the detection channel of the detector is a capillary.

6. The system according to claim 1, wherein the system comprises a gas inlet into the detection channel, which is situated below the optical axis of the light beam.

7. The system according to claim 5, wherein the capillary is fixed within a capillary guider comprising two connectors arranged on the optical axis of the light beam, wherein the first connector is configured to receive a first optical fiber that extends from the second light source and the second connector is configured to receive a second optical fiber that extends towards the second photodetector.

8. A method for isolating picoliter droplets comprising:
1) providing a system according to claim 1,
2) transporting a picoliter droplet in a carrier fluid towards the sorter,
3) selecting a picoliter droplet within the microfluidic chip based upon an optical signal obtained from said picoliter droplet,
4) transporting the selected picoliter droplet towards the detection channel,
5) detecting the passage of a selected picoliter droplet through the light beam in the detection channel due to a change of light intensity measured at the first photodetector,
6) triggering a movement of the detection channel and/or the collector when a passage of a picoliter droplet has been detected in step 5), and
7) depositing the picoliter droplet into a well.

9. The method according to claim 8, wherein the picoliter droplet comprises an aqueous buffer and a biological material selected from a group consisting of eukaryotic cells, prokaryotic cells, plant cells, viruses, proteins and nucleic acids.

10. The method according to claim 8, wherein part of the content of the well into which the picoliter droplet has been deposited in step 6) is extracted for a subsequent analysis and/or a scale-up of the content of the picoliter droplet by replicating a biological material.

11. The method according to claim 8, wherein in step 3), a fluorescent and/or a non-fluoresent image of the picoliter droplet is captured and processed for the sorting of the picoliter droplets.

12. The method according to claim 8, wherein in step 3), the emission of a fluorescent signal originating from a picoliter droplet is measured and is used as a selection criteria for the sorting of the picoliter droplet.

13. The method according to claim 8, wherein more than 10 picoliter droplets per second are sorted.

14. The method according to claim 8, wherein more than 100 picoliter droplets per second are sorted.

15. The method according to claim 8, wherein more than 1000 picoliter droplets per second are sorted.

16. The method according to claim 8, wherein the picoliter droplets isolated comprise a clonal population of cells in a culture medium.

17. The method according to claim 8, wherein the detection of a picoliter droplet in step 5) triggers a streaming of a gas into the detection channel via the gas inlet in order to dispense said picoliter droplet.

18. The system according to claim 1, wherein the detection channel is a glass capillary.

* * * * *